United States Patent
Nielsen et al.

(10) Patent No.: US 9,097,706 B2
(45) Date of Patent: **\*Aug. 4, 2015**

(54) INSECT-BASED EX VIVO MODEL FOR TESTING BLOOD-BRAIN BARRIER PENETRATION AND METHOD FOR EXPOSING INSECT BRAIN TO CHEMICAL COMPOUNDS

(75) Inventors: Peter Aadal Nielsen, Oxie (SE); Gunnar Andersson, Roestaanga (SE); Olga Andersson, Roestaanga (SE)

(73) Assignee: ENTOMOPHARM APS, Odense SV (DK)

( * ) Notice: Subject to any disclaimer, the term of this patent is extended or adjusted under 35 U.S.C. 154(b) by 10 days.

This patent is subject to a terminal disclaimer.

(21) Appl. No.: 13/387,088

(22) PCT Filed: Aug. 10, 2010

(86) PCT No.: PCT/EP2010/061585
§ 371 (c)(1),
(2), (4) Date: Jan. 25, 2012

(87) PCT Pub. No.: WO2011/018446
PCT Pub. Date: Feb. 17, 2011

(65) Prior Publication Data
US 2012/0122145 A1   May 17, 2012

Related U.S. Application Data

(60) Provisional application No. 61/233,150, filed on Aug. 12, 2009.

(51) Int. Cl.
*C12Q 1/00* (2006.01)
*G01N 33/50* (2006.01)

(52) U.S. Cl.
CPC ................... *G01N 33/5085* (2013.01)

(58) Field of Classification Search
CPC ................................. G01N 33/5085
USPC ........................................................... 435/4
See application file for complete search history.

(56) References Cited

U.S. PATENT DOCUMENTS

| | | |
|---|---|---|
| 7,332,159 B2 | 2/2008 | Labhasetwar et al. |
| 2005/0132425 A1 | 6/2005 | Lowe et al. |
| 2005/0214221 A1 | 9/2005 | Poss et al. |
| 2008/0025959 A1* | 1/2008 | Daneman et al. ............ 424/94.1 |

FOREIGN PATENT DOCUMENTS

| | | |
|---|---|---|
| WO | WO 2004/006854 A2 | 1/2004 |
| WO | WO 2010/031794 | 3/2010 |

OTHER PUBLICATIONS

Mokri-Hoayyed et al., 2008, J. Medical Microbiology, vol. 57, pp. 106-110.*
Mokri-Moayyed et al. (Jan. 2008, J. Med. Microbiology, vol. 57, pp. 106-110).*
Garberg et al. (2005, Toxicology in Vitro, vol. 19, pp. 299-334).*
Carlson et al. (2000. Annu. Rev. Entomol. vol. 45, pp. 151-174).*
Gullan et al. (2005, The Insects, An Outline of Entomology, 3rd Ed., pp. 30-37 and 56-58, including title pages).*
Josserand et al. (2006, J. Pharmacology and Exp. Therapeutics, vol. 316(1), pp. 79-86).*
Busch et al., "A Map of Octopaminergic Neurons in the *Drosophilia* Brain", *The Journal of Comparative Neurology*, vol. 513, 2009, pp. 643-667.
International Search Report and Written Opinion for International Application No. PCT/Ep2010/061585 mailed Nov. 8, 2010.
Jeibmann et al., "*Drosophila melanogaster* as a Model Organism of Brain Diseases", *International Journal of Molecular Science*, vol. 10, 2009, pp. 407-440.
Mayer et al., "Evolutionary Conservation of Vertebrate Blood-Brain Barrier Chemoprotective Mechanisms in *Drosophila*", *The Journal of Neuroscience*, 2009, pp. 3538-3550.
Mokri-Moayyed et al., "Development of a novel ex vivo insect model for studying virulence determinants of *Escherichia coli* K1", *Journal of Medical Microbiology*, vol. 57, 2008, pp. 106-110.
Mortazavi et al., "Novel model for the in vivo study of central nervous system infection due to *Acanthamoeba* spp. (T4 genotype)", *Journal of Medical Microbiology*, vol. 58, 2009, pp. 503-508.
Sarantseva et al., "Protein Transduction Domain Peptide Mediates Delivery to the Brain via the Blood-Brain Barrier in *Drosophila melanogaster*", *Biochemistry (Moscow) Supplement Series B: Biomedical Chemistry*, vol. 3, No. 2, 2009, pp. 149-155.
Carlson et al., "Blood barriers of the insect," *Annu. Rev. Entemol.* (2000) 45: 151-174.
Drobne et al., "In vivo screening to determine hazards of nanoparticles: Nanosized $TiO_2$", *Environmental Pollution*, vol. 157, 2009, pp. 1157-1164.
Fischer et al., "Nanotoxicity: the growing need for in vivo study", *Current Opinion in Biotechnology*, vol. 18, 2007, pp. 565-571.
Fortini et al., "Modeling human neurodegenerative diseases in *Drosophilia*," *TIG* (2000) 16 (4): 161-167.
Final Office Action from U.S. Appl. No. 13/060,619 mailed Jan. 30, 2013.
Hamamoto et al., "Silkworm as a model animal to evaluate drug candidate toxicity and metabolism", *Comparative Biochemistry and Physiology, Part C*, vol. 149, 2009, pp. 334-339.

(Continued)

*Primary Examiner* — Anoop Singh
*Assistant Examiner* — David A Montanari
(74) *Attorney, Agent, or Firm* — Merchant & Gould P.C.

(57) ABSTRACT

There is provided an ex-vivo insect screening model to accurately determine blood-brain barrier penetration of different chemical compounds in order to improve the compound screening procedures/processes in the early drug discovery process. This object offers many advantages relative to prior technologies since insect models are more reliable tools for the decision-making process than the existing in vitro models, and will speed up the drug screening process and reduce the late phase attrition rate. Moreover, it will reduce the number of mammals sacrificed during the drug discovery phase.

14 Claims, 1 Drawing Sheet

(56) References Cited

OTHER PUBLICATIONS

International Search Report and Written Opinion for International Application PCT/EP2010/061596 mailed Oct. 6, 2010.

Khan et al., "Novel model to study virulence determinants of *Escherichia coli* K1," *Infection and Immunity* (2007) 75 (12): 5735-5739. XP002557533.

Marsh et al., "Can files help humans treat neurodegenerative diseases?" *BioEssays* (2004) 26: 485-496.

Marsh et al., "*Drosophilia* in the study of neurodegenerative disease," *Neuron* (2006) 52: 169-178. XP002557534.

Non-Final Office Action from U.S. Appl. No. 13/060,619 mailed Aug. 29, 2012.

Non-Final Office Action from U.S. Appl. No. 13/060,619 mailed Jul. 16, 2013.

Non-Final Office Action from U.S. Appl. No. 13/387,094 mailed Feb. 12, 2013.

Olivier, "Drug Transport to Brain with Targeted Nanoparticles", *NeuroRx*, vol. 2, No. 1, 2005, pp. 108-119.

Parker et al., "Roles of glia in the *Drosophilia* nervous system," *Seminars in Cell & Developmental Biology* (2006) 17: 66-77.

Restriction Requirement Office Action from U.S. Appl. No. 13/060,619 mailed Jun. 21, 2012.

Restriction Requirement Office Action from U.S. Appl. No. 13/387,094 mailed Sep. 24, 2012.

Stork et al., "Organization and Function of the Blood-Brain Barrier in *Drosophila*", *The Journal of Neuroscience*, vol. 28, No. 3, 2008, pp. 587-597.

Warheit et al., "Development of a base set of toxicity tests using ultrafine $TiO_2$ particles as a component of nanoparticle risk management", *Toxicology Letters*, vol. 171, 2007, pp. 99-110.

Wilson, "Brain targeting PBCA nanoparticles and the blood-brain barrier", *Nanomedicine*, vol. 4, No. 5, 2009, pp. 499-502.

Wolf et al., "Invertebrate models of drug abuse," *J. Neurobiol.* (2003) 54: 161-178.

Form PCT/ISA/210 for corresponding International Application PCT/EP2009/062023.

Form PCT/ISA/220 for corresponding International Application PCT/EP2009/062023.

Form PCT/ISA/237 for corresponding International Application PCT/EP2009/062023.

Kim et al., "Blood-Brain Barrier Permeability during the Development of Experimental Bacterial Meningitis in the Rat", Experimental Neurology, 145:253-257 (1997).

Neuwelt et al., "Cerebrovascular permeability and delivery of gentamicin to normal brain and experimental brain abscess in rates", J. Neurosurg, 61:430-439 (Sep. 1984).

Strausbaugh et al., "Effect of Osmotic Blood-Brain Barrier Disruption on Gentamicin Penetration into the Cerebrospinal Fluid and Brains of Normal Rabbits", Antimicrobial Agents and Chemotherapy, 24(2):147-150 (Aug. 1983).

* cited by examiner

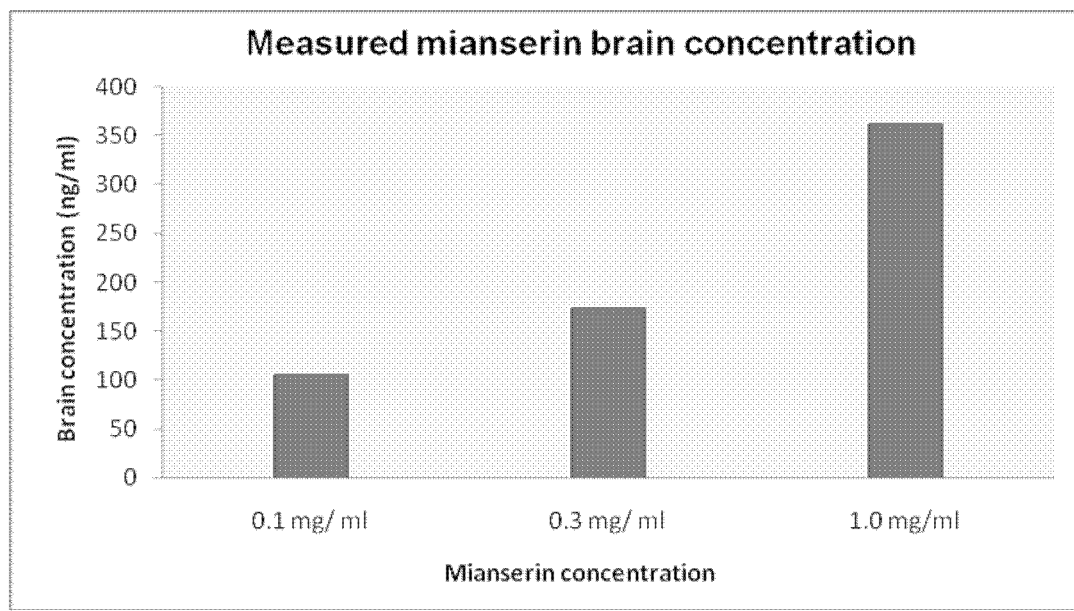

INSECT-BASED EX VIVO MODEL FOR TESTING BLOOD-BRAIN BARRIER PENETRATION AND METHOD FOR EXPOSING INSECT BRAIN TO CHEMICAL COMPOUNDS

This application is a National Stage Application of PCT/EP2010/061585, filed 10 Aug. 2010, which claims benefit of Ser. No. 61/233,150, filed 12 Aug. 2009 in the United States and which applications are incorporated herein by reference. To the extent appropriate, a claim of priority is made to each of the above disclosed applications.

FIELD OF THE INVENTION

The present invention is directed to an insect model that is aimed to reflect vertebrate blood-brain barrier (BBB) penetration. Investigation of BBB penetration is extremely important in drug discovery; successful CNS drugs have to cross the BBB, while BBB penetration may cause unwanted side effects for peripheral acting drugs.

Specifically, the present invention relates to the use of insects in screening for substances with a biological effect on the brain or central nervous system and/or effect on a disease or disorder of the brain or central nervous system. It further relates to use of such insects in screening for substances that have a desired biological activity and which do not cross the blood brain barrier.

BACKGROUND OF THE INVENTION

Pharmacologic remedy of many brain diseases is difficult because of the powerful drug exclusion properties of the blood-brain barrier (BBB). Chemical isolation of the vertebrate brain is achieved through the highly integrated, anatomically compact and functionally overlapping chemical isolation processes of the BBB. These include functions that need to be coordinated between tight diffusion junctions and unidirectionally acting xenobiotic transporters. Understanding of many of these processes has been hampered, because they have been experimentally difficult and expensive to disentangle in intact rodent models. Consequently, many of the processes are not well mimicked by in vitro or ex vivo BBB models.

In drug research it is extremely important to determine brain penetration both for drug candidates with CNS therapeutic potential but also for compounds which can cause CNS mediated side effects. There are in principle two strategies to measure brain penetration, a) determination of the rate of brain uptake at the initial state and b) the extent of brain exposure at the static state. The former is regarded as the most relevant because it is not compromised by metabolism, plasma binding or non specific brain binding due to the short exposure time. Because of their importance numerous methods have been developed to evaluate the rate of brain penetration. In situ brain perfusion, cell-based MDR1-MDCK assay and the PAMPA method are the most common assays in the pharmacological industry to determine BBB permeability. In situ brain perfusion is considered a golden standard method for measuring BBB permeability but in the pharmaceutical industry it does not fulfil the requirements of a method with high throughput and short-term feed back during the earliest step of drug discovery due to its labour intensity and high cost per tested candidate. For this reason the industry tend to use the high throughput but inaccurate in vitro models to assess BBB penetration.

In general, the in vitro, based, assays are regularly and routinely applied in the pharmaceutical early drug discovery phases and despite that there are major limitations by these assays most pharmaceutical companies use large batteries of in vitro screens. However, testing compounds in a large number of in vitro assays may not always reflect the in vivo behaviour. In fact, it is not unusual that compounds that have acceptable in vitro profiles turn out to have inadequate in vivo profiles. On the contrary, compounds may be discarded for wrong reasons.

Hence, there is a demand for intermediate models that are more reliable than in vitro models and at the same time faster and cheaper than traditional vertebrate in vivo models.

The vertebrate blood-brain barrier (BBB) represents the physiologic barrier between the brain tissue and blood vessels, which restricts the exchange of solutes and regulates absorption of exogenic agents (e.g. drugs) from the blood into the brain. The function of the central nervous system (CNS) requires a highly regulated extra-cellular environment. Anatomically the BBB in vertebrates is comprised of microvascular endothelia cells interconnected via highly specialized tight junctions (TJs), which provide a diffusion barrier and thus play a central role for permeability. Recently identified components of TJs include the claudins, a family of four-transmembrane-span proteins that are suggested to be responsible for the barrier-function of TJs (Turksen and Troy 2004). Penetration of BBB is one of the major hurdles in the development of successful CNS drugs. On the other hand, when penetration of the BBB occurs it may cause unwanted side effects for peripheral acting drugs (Schinkel 1999) (for review see Pardridge 2002).

BBB penetration is usually classified as chemistry- or biology-based. The chemistry-based penetration is linked to the lipid mediated passive diffusion, which depends on physiochemical properties of the molecule, i.e. small hydrophobic molecules tend to penetrate the BBB more readily than large and hydrophilic molecules. The biology-based penetration involves compounds that are substrates for the endogenous BBB influx or efflux transport systems, e.g. many small molecules (e.g. drugs) have shown to be substrates for the P-glycoprotein (P-gp) transporter. The P-gp's are transporter proteins located in the walls of the cells that make up the BBB (Schinkel 1999) and they are conserved among taxa as diverse as protozoa, plants, insects and mammals (Gaertner et. al. 1998). P-gp's are present in many cell-types and they play important roles in drug absorption, disposition, metabolism, and toxicity (Xia et al. 2006).

Obviously, it is crucial to have an understanding of the BBB penetration in drug discovery projects and preferably, this should be obtained without using excessive number of in vivo studies. Consequently, several in vitro absorption models are developed to predict the in vivo behaviour of test compounds. However, even complex in vitro models which include the P-gp transporter systems (Di and Kerns 2003, Summerfield et al. 2005) seem not to meet the intricate complexity of the BBB and therefore may not describe the in vivo behavior very well. The popular CaCo-2 model, developed to predict oral uptake, showed to be less useful for predicting brain penetration and the MDR1-MDCK assay, which is widely applied in industry, is mainly used to diagnose a Pgp efflux transport and recent studies have confirmed the low predictability of passive BBB permeability of this model (Summerfield et al., 2007). In an extensive BBB absorption study 22 compounds were tested in ten different in vitro BBB absorption models (Garberg 2005). None of the ten models showed correlation between in vitro and in vivo permeability. This indicates that specific BBB models not necessarily provide better prediction than non-BBB derived models. Furthermore, it was suggested that protein binding, blood-flow, metabolic stability and lipophilicity, as well as affinity for other transporters in the BBB are factors needed to be considered when predictions of in vivo brain distribution is to be made. Consequently, it seems as in vitro models are mainly suited for qualitative measurements of compounds that penetrates BBB by passive diffusion or compounds that undergo efflux via the P-gp transporter (Garberg 2005).

In vertebrates, a physically separate blood-brain barrier (BBB), primarily engineered into the single-cell layer vascular endothelium, provides an obstacle to chemical attack. At this interface, strong selective pressures have produced the integration of at least two very different cell biologic mechanisms to prevent free movement of small molecules between the humoral and CNS interstitial compartments. (Abbott, 2005; Daneman and Barres, 2005; Neuwelt et al., 2008; Zlokovic, 2008). BBB vascular endothelium cells impede the traffic of drugs by virtue of specialized lateral junction components, including tight junctions, and asymmetrically arrayed ATP binding cassette (ABC) transporters. Tight junctions prevent paracellular diffusion of charged molecules, and asymmetrically arrayed transporters actively expel lipophilic molecules back into the humoral space (Löscher and Potschka, 2005). Together, these complimentary systems prevent the majority of xenobiotics from acting on vertebrate nervous tissue (Pardridge, 2005). Although in vivo and in vitro BBB models have confirmed the importance of these two components (Schinkel et al., 1997; Nitta et al., 2003), substantial limitations hinder progress (Garberg et al., 2005). A powerful BBB model system should combine molecular genetic, genomic, chemical biology, and integrative physiology tools to probe CNS-specific chemoprotective physiology.

Recent research have shown that insects possess neural barriers that differs anatomically from the vertebrate barriers but also possess a number of highly important and relevant structures that is shared with the vertebrate barrier making the insect brain barrier a superior candidate for BBB permeability studies. Thus it has been shown that the insect barrier cells (glia) contain pleated septate and tight junctions nearly identical to the proteins that make up the vertebrate tight junctions (Wu and Beitel, 2004; Pardridge, 2005). Furthermore, it has been shown that insects possess a homology to the major ATP binding cassette (ABC) transporter (MDR/Pgp). It has also been shown that the active transporter homolog is localised at the hemolymph barrier, indicating that the subperineural glia in insects, like the vascular endothelium in vertebrates, possesses both tight junction barriers and active efflux transporters. These conclusions strengthen the utility of the insect BBB as a relevant model for screening and documentation of brain penetration in drug research. In further support of the functional relevance of the insect brain barrier model it has been shown in Drosophila that manipulation of the two principal barrier mechanisms by using measures relevant for the vertebrate barriers will open up both the diffusion and the transport barriers in Drosophila. Thus treatment of Drosophila with the known vertebrate MDR1/Pgp transport blocker Cyclosporin A (CsA) increased the ABC substrate in the Drosophila brain (Mayer et al., 2009) and osmotic manipulation of the grasshopper (L. migratoria) open up the diffusion barrier at similar concentration as is used in correspondent vertebrate studies (Andersson et al., 2009). Thus the coincident localization of the diffusion and the xenobiotic transport barriers demonstrate that insects combine vertebrate-like drug exclusion mechanisms to maintain a chemical barrier to the brain. These observations are the base for an ex vivo insect model with high utility in the early screening and documentation of candidate compounds in early drug discovery phase. In contrast to other models (e.g. in vitro models including the PAMPA model) our model is characterised by the properties that are the bases for an appropriate function of a brain barrier and in this sense highly relevant for prediction of brain penetration in vertebrates including human.

In CNS drug discovery there is a need for efficient screening of compounds aimed at targets within the CNS system. This screening is preferentially performed in insect models with intact BBB function and will contribute to a positive selection of compounds penetrating the BBB. Such screening comprises low molecular weight compounds within a number of indications (e.g. pain, epilepsy, Parkinson, schizophrenia, Alzheimer, sleep disorders, anxiety, depression, eating disorders, drug abuse including smoking).

SUMMARY OF THE INVENTION

The object of the present invention is to develop an ex-vivo insect screening model to accurately determine blood-brain barrier penetration of different chemical compounds in order to improve the compound screening procedures/processes in the early drug discovery phase. This object offers many advantages relative to prior technologies since insect models are more reliable tools for the decision-making process than the existing in vitro models, and will speed up the drug screening process and reduce the late phase attrition rate. Moreover, it will reduce the number of mammals sacrificed during the drug discovery phase. Finally, it is an object of the present invention that only the penetration trough the blood-brain barrier is determined, without any interference from liver metabolism, accumulation in other tissues etc.

Accordingly, there is provided a method of conducting blood-brain barrier penetration studies of a chemical compound in an insect, said method comprising the steps:
optionally anesthetizing the insect;
fixing the head of the insect;
dissecting out the dorsal part of the insect head so as to expose the brain, eyes, antennas, and nerve associations;
treating the brain while in its cuticle shell with a solution of the chemical compound; and
removing the brain from its cuticle;
washing and homogenising the brain;
determining the concentration of the chemical compound in the homogenised brain material; and
calculating the penetration of the chemical compound through the blood-brain barrier.

In a preferred embodiment of the present invention albumin is added to the solution of the chemical compound to introduce the plasma protein binding and the effect of the plasma protein binding upon the chemical compound's BBB penetration (free vs. protein bound chemical compounds).

Preferable the concentration of the chemical compound is determined by LC/MS. In this respect the determination of the concentration of the chemical compound is performed by homogenizing or ultra sound disintegration (UD) of the dissected brains, and analyzing the concentration of the test agent in the homogenate by liquid chromatography with mass spectrometric detection of the eluted compounds In order to ensure optimum penetration of the chemical compound the brain is treated with the solution of the chemical compound for a period of 1 min.-6 hrs. In a particularly preferred embodiment of the present invention the neural lamella of the brain is removed before the brain is subjected to homogenization or UD.

In addition to the method of the present invention there is further provided a model for conducting blood-brain barrier penetration studies of a chemical compound, said model obtained by a method comprising the steps:
optionally anesthetizing an insect;
fixing the head of the insect; and
dissecting out the dorsal part of the insect head so as to expose the brain, eyes, antennas, and nerve associations.

In a particularly preferred embodiment of this model the neural lamella of the brain is removed.

The method of the present invention permits the exposure to an insect brain of a test chemical compound solution at a stable concentration during the entire period of exposure. As appears from above the insect model used in the method consists of the dorsal part of the insect head dissected out to consist of the brain, eyes, antennas and the nerve associations between these sense organs. Still in its cuticle shell the brain will be treated with different test compound for various times. The penetration of the test chemical compound over the BBB into the brain is determined as the concentration (amount) of the chemical compound measured in the isolated brain and preferably determined by LC/MS. The model is aimed as an early stage test of chemical compounds, in particular drugs, for their ability to cross the BBB at a well defined and constant exposure concentration.

The present invention is applicable for testing chemical compounds' ability to pass the BBB. This approach has particular relevance when testing if a given drug may pass the BBB. Thus, the present invention is particularly useful when the chemical compound is a drug, especially a CNS active drug.

The present invention is thus able to provide for the first time rational strategies for screening compounds for neurological indications, as well as generating a simple in vivo system for determining a compound's brain penetration. The present invention is also able to provide a rational screening of compounds in insect models mimicking BBB dysfunction as a consequence of neurological disorders.

Drug discovery is a long and costly process, requiring vast amount of chemical and biological resources. In the present invention the possibilities to use insects as model systems have been thoroughly exploited in order to improve compound selection processes and reduce the costs during the drug discovery phase. Based on recent discoveries the inventors have fully contemplated that insect models of the present invention provide a better foundation than the existing in vitro models for selection of compounds to be tested in vertebrates.

Various aspects and embodiments the present invention provides the subject-matter set out in the claims below.

The invention is generally applicable to any of a drug discovery programs targeting a variety of diseases and disorders, specifically degenerative disorders, including: Parkinson's Disease, Alzheimer's Disease, Huntington's Disease, Diseases with motor neuron inclusions, Tauopathies, Corticobasal degeneration; Neuropsychiatric disorders, including: Depression Bipolar disease, Schizophrenia, Anxiety, and Aggression. Moreover, the invention is applicable for drug discovery programs targeting peripheral targets where no CNS driven side effect can be tolerated or screening of chemical compounds which effects on CNS functions is unknown.

Thus, the invention is equally applicable to screening for chemical compounds which exert a biological effect that alters an activity or function in the central nervous system, brain or eye, whether normal or subject to a disease or disorder, as to screening for agents which exert a biological effect that is ameliorative of a sign or symptom of a disease or disorder. Moreover, the present invention offers the possibility to test whether or not peripheral acting drugs and toxic agents, such as pesticides, unintentionally penetrate the BBB.

Following identification of a test substance with desired biological activity using a method in accordance with any aspect or embodiment of the present invention the test substance may be formulated into a composition comprising at least one additional component, for example a pharmaceutically acceptable vehicle, carrier or excipient.

BRIEF DESCRIPTION OF THE DRAWING

FIG. 1 shows that the mianserin brain concentration increases when the brain is exposed to higher mianserin concentrations

DETAILED DESCRIPTION OF THE INVENTION

The present invention provides new methodology for screening chemical agent's ability to penetrate the BBB. The invention is generally particular useful for high throughput screening for agents developed in drug discovery programs targeting a variety of diseases and disorders, specifically degenerative disorders, including: Parkinson's Disease, Alzheimer's Disease, Huntington's Disease, Diseases with motor neuron inclusions, Tauopathies, Corticobasal degeneration Neuropsychiatric disorders, including: Depression Bipolar disease, Schizophrenia, Anxiety, and Aggression. Moreover, the invention is applicable for drug discovery programs targeting peripherical targets where no CNS driven side effect can be tolerated. Moreover, the present invention is applicable in the screening of agents developed in drug discovery programs targeting eating disorders and sleep disorders etc.

A drug in accordance with the present invention is defined in its broadest scope as a chemical compound that, when absorbed into the body of a living organism, alters normal bodily function. More specifically, a drug in accordance with the present invention is a chemical compound that may be used in the treatment, cure, prevention, or diagnosis of disease or used to otherwise to enhance physical or mental well-being. Of particular interest in accordance with the present invention are psychoactive drugs, which are chemical compounds that cross the BBB and acts primarily upon the central nervous system where it alters brain function, resulting in changes in perception, mood, consciousness, cognition and behavior.

The present invention relates to but is not restricted to the use of insects selected from the following orders: (Taxonomy according to: Djurens Värld, Ed B. Hanström; Förlagshuset Norden AB, Malmö, 1964):

| Order | Suborder/family | Comment |
|---|---|---|
| Dictyoptera | Blattoidea | Cockroach |
| | Mantoidea | |
| Orthoptera | Grylloidea | Crickets |
| | Acridoidea | Grasshoppers |
| Cheleutoptera | | Stick insects |
| Lepidoptera | | Moths |
| Hymenoptera | Formicoidea | Ants |
| | Vespoidea | Wasps |
| | Apoidea | Bee like Hymenopterans |
| | Bombinae | Bumble-bees |
| | Apine | Proper bees |
| Odonata | | Dragonflies |
| Diptera | Nematocera | Mosquitos |
| | Brachycera | Flies E.g *Drosophila* |

In particular the invention relates to insect species selected from Blattoidea, Acridoidea, Cheleutoptera, Brachycera and Lepidoptera and most particular to the Acridoidea (*Locusta migratoria* and *Schistocera gregaria*). The invention will also relate to the following orders comprising insect species relevant for the method of the present invention:

| Order | Suborder/family | Comment |
|---|---|---|
| Ephemerida | | Mayflies |
| Plecoptera | | |
| Dermoptera | Forficuloidea | Earwigs |
| Homoptera | Cicadinea | Cicadas |
| | Aphidine | Plant-louse |
| Heteroptera | | Hemipteran |
| Coleoptera | | Beetles |
| Trichoptera | | Caddis fly |

The present invention preferably uses large insects, such as the migratoty locust, *Locusta migratoria* and the desert locust, *Schistocera gregaria* or cockroach where it is feasible to feed and inject drugs and subsequently take hemolymph samples and dissect brain tissues, for analyses. The locust has been used to develop screening models to determine BBB penetration of different therapeutic drugs and compare this model with existing literature data from conventional in vivo or in situ vertebrate studies.

EXAMPLES

1. In a preferred embodiment of the present invention the insects are selected from the order Acridoidea and specifically *Locusta migratoria* and *Schistocera gregaria* are used. The insects may be obtained from local suppliers or bred in house. The grasshoppers were reared under crowded conditions at 28° C. and a 12:12 dark:light photocycle and fed fresh grass and bran. Before experiments the grasshoppers were fed ecologically cultivated wheat for two weeks. Animals used are adult males (in some experiments females) between two to four weeks after adult emergence. A cut is made through the frontal part of the locust head comprising the most frontal parts including the antennae, the compound eyes, the brain and all neural connections between the brain and the antennae and the eyes. This preparation in its cuticle shell is placed in a well of a microtitre plate containing the test solution. After various times of exposure the preparation is washed in saline and the brain is dissected under microscope with fine forceps. The neural lamella surrounding the brain is removed in saline and the brain is then UD in saline, centrifuged and the supernatant frozen until analyses. Drug concentration is analysed by HPLC, LC/MSMS or other methods.

2. In a preferred embodiment of present invention the insects are selected from the order Acridoidea and specifically *Locusta migratoria* and *Schistocera gregaria* are used. The insects may be obtained from local suppliers or bred in house. The grasshoppers were reared under crowded conditions at 28° C. and a 12:12 dark:light photocycle and fed fresh grass and bran. Before experiments the grasshoppers were fed ecologically cultivated wheat for two weeks. Animals used are adult males (in some experiments females) between two to four weeks after adult emergence. A cut is made through the frontal part of the locust head comprising the most frontal parts including the antennae, the compound eyes, the brain and all neural connections between the brain and the antennae and the eyes. This preparation in its cuticle shell is placed in a well of a microtitre plate containing a test solution comprising the substance of interest and 4.2% bovine serum albumin. After various times of exposure the preparation is washed in saline and the brain is dissected under microscope with fine forceps. The neural lamella surrounding the brain is removed in saline and the brain is then UD in saline, centrifuged and the supernatant frozen until analyses. Drug concentration is analysed by HPLC, LC/MSMS or other methods.

In the following the present invention is exemplified in further detail.

Example A

A cut was made through the frontal part of the head of adult female *locusta migratoria*. Each brain in its cuticle shell was placed in a 0.12 mg/ml mianserin solution for 5 minutes. The brain was prepared in saline and removed from the cuticle shell and three brains were placed in each test tube containing 100 ul distilled H2O. 200 ul ACN was added to each tube and the tubes were placed in a sonicator and the brains were disintegrated by approximately 5 seconds of sonication. The samples containing the disintegrated brains were centrifuged for 5 minutes (10000 g at 4° C.). 100 ul of the supernatant was placed in a new test tube and an average mianserin concentration of 3 ug/ml was measured by LCMS.

Example B

A cut was made through the frontal part of the head of adult female *locusta migratoria*. Each brain in its cuticle shell was placed in a 0.12 mg/ml mianserin solution for 15 minutes. The brain was prepared in saline and removed from the cuticle shell and three brains were placed in each test tube containing 100 ul distilled H2O. 200 ul ACN was added to each tube and tubes were placed in a sonicator and the brains were disintegrated by approximately 5 seconds of sonication. The samples containing the disintegrated brains were centrifuged for 5 minutes (10000 g at 4° C.). 100 ul of the supernatant was placed in a new test tube and an average mianserin concentration of 2.2 ug/ml was measured by LCMS.

Example C

A cut was made through the frontal part of the head of adult female *locusta migratoria*. Each brain in its cuticle shell was placed in a 0.12 mg/ml mianserin solution for 5 minutes. The brain was prepared in saline and removed from the cuticle shell. The brains were washed in Saline. After wash three brains were placed in each test tube containing 100 ul distilled H2O. 200 ul ACN was added to each tube and the tubes were placed in a sonicator and the brains were disintegrated by approximately 5 seconds of sonication. The samples containing the disintegrated brains were centrifuged for 5 minutes (10000 g at 4° C.). 100 ul of the supernatant was placed in a new test tube and an average mianserin concentration of 2.4 ug/ml was measured by LCMS.

Example D

A cut was made through the frontal part of the head of adult female *locusta migratoria*. Each brain in its cuticle shell was placed in a 0.12 mg/ml mianserin solution for 15 minutes. The brain was prepared in saline and removed from the cuticle shell. The brains were washed in Saline. After wash three brains were placed in a test tube containing 100 ul distilled H2O. 200 ul ACN was added to each tube and the tubes were placed in each sonicator and the brains were disintegrated by approximately 5 seconds of sonication. The samples containing the disintegrated brains were centrifuged for 5 minutes (10000 g at 4° C.). 100 ul of the supernatant was placed in a new test tube and the average mianserin concentration of 1.3 ug/ml was measured by LCMS.

Example E

A cut was made through the frontal part of the head of adult female *locusta migratoria*. Each brain in its cuticle shell was placed in a 0.12 mg/ml mianserin solution for 5 minutes. The brain was prepared in saline and removed from the cuticle shell. To stain the neural lamella Evans Blue was added and the neural lamella was removed. Three brains were placed in each test tube containing 100 ul distilled H2O. 200 ul ACN was added to each tube and the tubes were placed in a sonicator and the brains were disintegrated by approximately 5 seconds of sonication. The samples containing the disintegrated brains were centrifuged for 5 minutes (10000 g at 4° C.). 100 ul of the supernatant was placed in a new test tube and an average mianserin concentration of 309 ng/ml was measured by LCMS.

From example A-E it can be concluded that mianserin permeate the grasshopper BBB but it can even be seen that the BBB still works as a regulator preventing free passage of mianserin from the exterior to the brain. Moreover, these examples shows that compound material stick to the neural lamella and this cannot be removed by washing but it requires removal of the lamella prior to the compound quantification by LCMS.

Example F

A cut was made through the frontal part of the head of the adult *locusta migratoria*. Each brain in its cuticle shell was placed in a 0.9 mg/ml mianserin solution for 5 minutes. The brain was prepared in saline and removed from the cuticle shell. Three brains were placed in a test tube containing 100 ul PBS. 200 ul ACN was added to each tube. The tubes were placed in a sonicator and the brains were disintegrated by approximately 5 seconds of sonication. The samples containing the disintegrated brains were centrifuged for 5 minutes (10000 g at 4° C.). 100 ul of the supernatant was placed in a new test tube and the average mianserin concentration of 1.3 ug/ml was measured by LCMS.

Example G

A cut was made through the frontal part of the head of the adult *locusta migratoria*. Each brain in its cuticle shell was placed in a 0.9 mg/ml mianserin solution for 5 minutes. The brain was prepared in saline and removed from the cuticle shell. To stain the neural lamella Evans Blue was added and the neural lamella was removed. Three brains were placed in each test tube containing 100 ul PBS. 200 ul ACN was added to each tube. The tubes were placed in a sonicator and the brains were disintegrated by approximately 5 seconds of sonication. The samples containing the disintegrated brains were centrifuged for 5 minutes (10000 g at 4° C.). 100 ul of the supernatant was placed in a new test tube and the average mianserin concentration of 0.6 ug/ml was measured by LCMS.

Example H

A cut was made through the frontal part of the head of the adult *locusta migratoria*. Each brain in its cuticle shell was placed in a 0.1 mg/ml mianserin solution for 5 minutes. The brain was prepared in saline and removed from the cuticle shell. Three brains were placed in a test tube containing 100 ul PBS. 200 ul ACN was added to each tube. The tubes were placed in a sonicator and the brains were disintegrated by approximately 5 seconds of sonication. The samples containing the disintegrated brains were centrifuged for 5 minutes (10000 g at 4° C.). 100 ul of the supernatant was placed in a new test tube and the average mianserin concentration of 217 ng/ml was measured by LCMS.

Example I

A cut was made through the frontal part of the head of the adult *locusta migratoria*. Each brain in its cuticle shell was placed in a 0.1 mg/ml mianserin solution for 5 minutes. The brain was prepared in saline and removed from the cuticle shell. To stain the neural lamella Evans Blue was added and the neural lamella was removed. Three brains were placed in each test tube containing 100 ul PBS. 200 ul ACN was added to each tube. The tubes were placed in a sonicator and the brains were disintegrated by approximately 5 seconds of sonication. The samples containing the disintegrated brains were centrifuged for 5 minutes (10000 g at 4° C.). 100 ul of the supernatant was placed in a new test tube and the average mianserin concentration of 127 ng/ml was measured by LCMS.

Example F-I show that inclusion of the neural lamella has a large impact on the measured brain concentration. In the 0.9 mg/ml mianserin solution the [with lamella]/[without lamella] ratio is 2.3 while the ratio when using the 0.1 mg/ml mianserin solution is 1.7, i.e. the ratios are at similar levels. Moreover, the results show that the brain concentration increases when the brains are exposed to higher concentrations of the solution.

Example J

A cut was made through the frontal part of the head of the adult *locusta migratoria*. Each brain was placed for 5 minutes in a microtiter well with an approximately 0.95 mg/ml solution of mianserin. To stain the neural lamella Evans Blue was added and the neural lamella was removed. Two brains are placed in each test tube and 100 ul distilled H2O and 200 ul ACN is added. The tubes were placed in a sonicator and the brains were disintegrated by approximately 5 seconds of sonication. The samples containing the disintegrated brains were centrifuged for 5 minutes (10000 g at 4° C.). 100 ul of the supernatant was placed in a new test tube and the average mianserin concentration of 1439 ng/ml was measured by LCMS.

Example K

A cut was made through the frontal part of the head of the adult *locusta migratoria*. Each brain was placed for 5 minutes in a microtiter well with an approximately 0.9 mg/ml solution of a trazodone. To stain the neural lamella Evans Blue was added and the neural lamella was removed. Two brains are placed in each test tube and 100 ul distilled H2O and 200 ul ACN is added. The tubes were placed in a sonicator and the brains were disintegrated by approximately 5 seconds of sonication. The samples containing the disintegrated brains were centrifuged for 5 minutes (10000 g at 4° C.). 100 ul of the supernatant was placed in a new test tube and the average trazodone concentration of 1317 ng/ml was measured by LCMS.

Example L

A cut was made through the frontal part of the head of the adult *locusta migratoria*. Each brain was placed for 5 minutes in a microtiter well with an approximately 0.67 mg/ml solution of a buspirone. To stain the neural lamella Evans Blue was added and the neural lamella was removed. Two brains are placed in each test tube and 100 ul distilled H2O and 200 ul ACN is added. The tubes were placed in a sonicator and the brains were disintegrated by approximately 5 seconds of sonication. The samples containing the disintegrated brains were centrifuged for 5 minutes (10000 g at 4° C.). 100 ul of the supernatant was placed in a new test tube and the average buspirone concentration of 909 ng/ml was measured by LCMS.

Example M

A cut was made through the frontal part of the head of the adult *locusta migratoria*. Each brain was placed for 5 minutes in a microtiter well with an approximately 0.78 mg/ml solution of a caffeine. To stain the neural lamella Evans Blue was added and the neural lamella was removed. Two brains are placed in each test tube and 100 ul distilled H2O and 200 ul ACN is added. The tubes were placed in a sonicator and the brains were disintegrated by approximately 5 seconds of sonication. The samples containing the disintegrated brains were centrifuged for 5 minutes (10000 g at 4° C.). 100 ul of the supernatant was placed in a new test tube and the average caffeine concentration of 1533 ng/ml was measured by LCMS.

Example N

A cut was made through the frontal part of the head of the adult *locusta migratoria*. Each brain was placed for 5 minutes in a microtiter well with an approximately 0.72 mg/ml solution of a propranolol. To stain the neural lamella Evans Blue was added and the neural lamella was removed. Two brains are placed in each test tube and 100 ul distilled H2O and 200 ul ACN is added. The tubes were placed in a sonicator and the brains were disintegrated by approximately 5 seconds of sonication. The samples containing the disintegrated brains were centrifuged for 5 minutes (10000 g at 4° C.). 100 ul of the supernatant was placed in a new test tube and the average propranolol concentration of 674 ng/ml was measured by LCMS.

Example O

A cut was made through the frontal part of the head of the adult *locusta migratoria*. Each brain was placed for 5 minutes in a microtiter well with an approximately 0.93 mg/ml solution of a colchicine. To stain the neural lamella Evans Blue was added and the neural lamella was removed. Two brains are placed in each test tube and 100 ul distilled H2O and 200 ul ACN is added. The tubes were placed in a sonicator and the brains were disintegrated by approximately 5 seconds of sonication. The samples containing the disintegrated brains were centrifuged for 5 minutes (10000 g at 4° C.). 100 ul of the supernatant was placed in a new test tube and the average colchicine concentration of 297 ng/ml was measured by LCMS.

Example P

A cut was made through the frontal part of the head of the adult *locusta migratoria*. Each brain was placed for 5 minutes in a microtiter well with an approximately 0.2 mg/ml solution of a atenolol. To stain the neural lamella Evans Blue was added and the neural lamella was removed. Two brains are placed in each test tube and 100 ul distilled H2O and 200 ul ACN is added. The tubes were placed in a sonicator and the brains were disintegrated by approximately 5 seconds of sonication. The samples containing the disintegrated brains were centrifuged for 5 minutes (10000 g at 4° C.). 100 ul of the supernatant was placed in a new test tube and the average atenolol concentration of 23 ng/ml was measured by LCMS.

Example J-P shows that the CNS active compounds (mianserin, caffeine, trazodone, buspirone, and propranolol) permeate the grasshopper BBB to a much larger extent than peripheral acting drugs (i.e. colchicine and atenolol). Thus, dissecting the grasshopper brain and placing the brain in a microtiter well containing a solution of a compound of interest is a useful model for determining whether the compound of interest permeate the vertebrate BBB.

Example Q

A cut was made through the frontal part of the head of the adult *locusta migratoria*. Each brain was placed for 5 minutes in a microtiter well with an approximately 0.1 mg/ml solution of mianserin. To stain the neural lamella Evans Blue was added and the neural lamella was removed. Two brains are placed in each test tube and 100 ul distilled H2O and 200 ul ACN is added. The tubes were placed in a sonicator and the brains were disintegrated by approximately 5 seconds of sonication. The samples containing the disintegrated brains were centrifuged for 5 minutes (10000 g at 4° C.). 100 ul of the supernatant was placed in a new test tube and the average mianserin concentration of 105 ng/ml was measured by LCMS.

Example R

A cut was made through the frontal part of the head of the adult *locusta migratoria*. Each brain was placed for 5 minutes in a microtiter well with an approximately 0.3 mg/ml solution of mianserin. To stain the neural lamella Evans Blue was added and the neural lamella was removed. Two brains are placed in each test tube and 100 ul distilled H2O and 200 ul ACN is added. The tubes were placed in a sonicator and the brains were disintegrated by approximately 5 seconds of sonication. The samples containing the disintegrated brains were centrifuged for 5 minutes (10000 g at 4° C.). 100 ul of the supernatant was placed in a new test tube and the average mianserin concentration of 174 ng/ml was measured by LCMS.

Example S

A cut was made through the frontal part of the head of the adult *locusta migratoria*. Each brain was placed for 5 minutes in a microtiter well with an approximately 1 mg/ml solution of mianserin. To stain the neural lamella Evans Blue was added and the neural lamella was removed. Two brains are placed in each test tube and 100 ul distilled H2O and 200 ul ACN is added. The tubes were placed in a sonicator and the brains were disintegrated by approximately 5 seconds of sonication. The samples containing the disintegrated brains were centrifuged for 5 minutes (10000 g at 4° C.). 100 ul of the supernatant was placed in a new test tube and the average mianserin concentration of 362 ng/ml was measured by LCMS.

Example Q-S shows the mianserin brain concentration increases when the brain is exposed to higher mianserin concentrations (see FIG. 1).

Example T

A cut was made through the frontal part of the head of the adult *locusta migratoria*. Each brain was placed for 5 minutes in a microtiter well with an approximately 0.001 mg/ml solution of quinidine. To stain the neural lamella Evans Blue was added and the neural lamella was removed. Two brains are placed in each test tube and 50 ul distilled H2O and 100 ul ACN is added. The tubes were placed in a sonicator and the brains were disintegrated by approximately 5 seconds of sonication. The samples containing the disintegrated brains were centrifuged for 5 minutes (10000 g at 4° C.). 100 ul of the supernatant was placed in a new test tube and the average quinidine concentration measured by LCMS was below detection level

Example U

A cut was made through the frontal part of the head of the adult *locusta migratoria*. Each brain was placed for 5 minutes in a microtiter well with an approximately 0.01 mg/ml solution of quinidine. To stain the neural lamella Evans Blue was added and the neural lamella was removed. Two brains are placed in each test tube and 50 ul distilled H2O and 100 ul ACN is added. The tubes were placed in a sonicator and the brains were disintegrated by approximately 5 seconds of sonication. The samples containing the disintegrated brains were centrifuged for 5 minutes (10000 g at 4° C.). 100 ul of the supernatant was placed in a new test tube and the average quinidine concentration measured by LCMS was below detection level.

Example V

A cut was made through the frontal part of the head of the adult *locusta migratoria*. Each brain was placed for 5 minutes in a microtiter well with an approximately 0.1 mg/ml solution of quinidine. To stain the neural lamella Evans Blue was added and the neural lamella was removed. Two brains are placed in each test tube and 50 ul distilled H2O and 100 ul ACN is added. The tubes were placed in a sonicator and the brains were disintegrated by approximately 5 seconds of sonication. The samples containing the disintegrated brains were centrifuged for 5 minutes (10000 g at 4° C.). 100 ul of the supernatant was placed in a new test tube and the average quinidine concentration was of 47 ng/ml was measured by LCMS.

Example W

A cut was made through the frontal part of the head of the adult *locusta migratoria*. Each brain was placed for 5 minutes in a microtiter well with an approximately 1.0 mg/ml solution of quinidine. To stain the neural lamella Evans Blue was added and the neural lamella was removed. Two brains are placed in each test tube and 50 ul distilled H2O and 100 ul ACN is added. The tubes were placed in a sonicator and the brains were disintegrated by approximately 5 seconds of sonication. The samples containing the disintegrated brains were centrifuged for 5 minutes (10000 g at 4° C.). 100 ul of the supernatant was placed in a new test tube and the average quinidine concentration was of 812 ng/ml was measured by LCMS.

Example X

A cut was made through the frontal part of the head of the adult *locusta migratoria*. Each brain was placed for 5 minutes in a microtiter well containing a mixture of verapamil (0.5 mg/ml) and quinidine (0.001 mg/ml). To stain the neural lamella Evans Blue was added and the neural lamella was removed. Two brains are placed in each test tube and 50 ul distilled H2O and 100 ul ACN is added. The tubes were placed in a sonicator and the brains were disintegrated by approximately 5 seconds of sonication. The samples containing the disintegrated brains were centrifuged for 5 minutes (10000 g at 4° C.). 100 ul of the supernatant was placed in a new test tube and the average quinidine concentration was of 3 ng/ml was measured by LCMS.

Example Y

A cut was made through the frontal part of the head of the adult *locusta migratoria*. Each brain was placed for 5 minutes in a microtiter well containing a mixture of verapamil (0.5 mg/ml) and quinidine (0.01 mg/ml). To stain the neural lamella Evans Blue was added and the neural lamella was removed. Two brains are placed in each test tube and 50 ul distilled H2O and 100 ul ACN is added. The tubes were placed in a sonicator and the brains were disintegrated by approximately 5 seconds of sonication. The samples containing the disintegrated brains were centrifuged for 5 minutes (10000 g at 4° C.). 100 ul of the supernatant was placed in a new test tube and the average quinidine concentration was of 11 ng/ml was measured by LCMS.

Example Z

A cut was made through the frontal part of the head of the adult *locusta migratoria*. Each brain was placed for 5 minutes in a microtiter well containing a mixture of verapamil (0.5 mg/ml) and quinidine (0.1 mg/ml). To stain the neural lamella Evans Blue was added and the neural lamella was removed. Two brains are placed in each test tube and 50 ul distilled H2O and 100 ul ACN is added. The tubes were placed in a sonicator and the brains were disintegrated by approximately 5 seconds of sonication. The samples containing the disintegrated brains were centrifuged for 5 minutes (10000 g at 4° C.). 100 ul of the supernatant was placed in a new test tube and the average quinidine concentration was of 52 ng/ml was measured by LCMS.

Example AA

A cut was made through the frontal part of the head of the adult *locusta migratoria*. Each brain was placed for 5 minutes in a microtiter well containing a mixture of verapamil (0.5 mg/ml) and quinidine (1 mg/ml). To stain the neural lamella Evans Blue was added and the neural lamella was removed. Two brains are placed in each test tube and 50 ul distilled H2O and 100 ul ACN is added. The tubes were placed in a sonicator and the brains were disintegrated by approximately 5 seconds of sonication. The samples containing the disintegrated brains were centrifuged for 5 minutes (10000 g at 4° C.). 100 ul of the supernatant was placed in a new test tube and the average quinidine concentration was of 684 ng/ml was measured by LCMS.

Example T-AA shows when the locust brain is exposed to low concentrations of quinidine (0.001 mg/ml and 0.01) there is no uptake of quinidine in the locust brain but at higher concentrations there was there is a dose related increase, Quinidine is a Pgp-efflux substrate and the results shows that the Pgp efflux transporter is saturated at high quinidine concentrations resulting in an increased uptake. Co-treatment with the Pgp inhibitor verapamil and the Pgp substrate quinidine, significantly increased the uptake of quinidine at the low dose range while the uptake was unaffected at the high dose where the Pgp proteins are expected to be saturated.

Example AB

A cut was made through the frontal part of the head of the Blattodea. Each brain was placed for 5 minutes in a microtiter well with an approximately 1.0 mg/ml solution of trazodone. To stain the neural lamella Evans Blue was added and the neural lamella was removed. Two brains are placed in each test tube and 50 ul distilled H2O and 100 ul ACN is added. The tubes were placed in a sonicator and the brains were disintegrated by approximately 5 seconds of sonication. The samples containing the disintegrated brains were centrifuged for 5 minutes (10000 g at 4° C.). 100 ul of the supernatant was placed in a new test tube and the average trazodone concentration was of 768 ng/ml was measured by LCMS.

Example AC

A cut was made through the frontal part of the head of the Blattodea. Each brain was placed for 5 minutes in a microtiter well with an approximately 0.1 mg/ml solution of trazodone. To stain the neural lamella Evans Blue was added and the neural lamella was removed. Two brains are placed in each test tube and 50 ul distilled H2O and 100 ul ACN is added. The tubes were placed in a sonicator and the brains were disintegrated by approximately 5 seconds of sonication. The samples containing the disintegrated brains were centrifuged for 5 minutes (10000 g at 4° C.). 100 ul of the supernatant was placed in a new test tube and the average trazodone concentration was of 127 ng/ml was measured by LCMS.

Example AD

A cut was made through the frontal part of the head of the Blattodea. Each brain was placed for 5 minutes in a microtiter well with an approximately 1.0 mg/ml solution of atenolol. To stain the neural lamella Evans Blue was added and the neural lamella was removed. Two brains are placed in each test tube and 50 ul distilled H2O and 100 ul ACN is added. The tubes were placed in a sonicator and the brains were disintegrated by approximately 5 seconds of sonication. The samples containing the disintegrated brains were centrifuged for 5 minutes (10000 g at 4° C.). 100 ul of the supernatant was placed in a new test tube and the average atenolol concentration was of 294 ng/ml was measured by LCMS.

Example AE

A cut was made through the frontal part of the head of the Blattodea. Each brain was placed for 5 minutes in a microtiter well with an approximately 0.1 mg/ml solution of atenolol. To stain the neural lamella Evans Blue was added and the neural lamella was removed. Two brains are placed in each test tube and 50 ul distilled H2O and 100 ul ACN is added. The tubes were placed in a sonicator and the brains were disintegrated by approximately 5 seconds of sonication. The samples containing the disintegrated brains were centrifuged for 5 minutes (10000 g at 4° C.). 100 ul of the supernatant was placed in a new test tube and the average atenolol concentration was of 27 ng/ml was measured by LCMS.

Example AF

A cut was made through the frontal part of the head of the Blattodea. Each brain was placed for 5 minutes in a microtiter well with an approximately 1.0 mg/ml solution of caffeine. To stain the neural lamella Evans Blue was added and the neural lamella was removed. Two brains are placed in each test tube and 50 ul distilled H2O and 100 ul ACN is added. The tubes were placed in a sonicator and the brains were disintegrated by approximately 5 seconds of sonication. The samples containing the disintegrated brains were centrifuged for 5 minutes (10000 g at 4° C.). 100 ul of the supernatant was placed in a new test tube and the average caffeine concentration was of 1028 ng/ml was measured by LCMS.

Example AG

A cut was made through the frontal part of the head of the Blattodea. Each brain was placed for 5 minutes in a microtiter well with an approximately 0.1 mg/ml solution of caffeine. To stain the neural lamella Evans Blue was added and the neural lamella was removed. Two brains are placed in each test tube and 50 ul distilled H2O and 100 ul ACN is added. The tubes were placed in a sonicator and the brains were disintegrated by approximately 5 seconds of sonication. The samples containing the disintegrated brains were centrifuged for 5 minutes (10000 g at 4° C.). 100 ul of the supernatant was placed in a new test tube and the average caffeine concentration was of 152 ng/ml was measured by LCMS.

Example AB-AG shows that the CNS active compounds (caffeine and trazodone) permeate the Blattodea BBB to a much larger extent than atenolol, which is a peripheral acting drug. Thus, dissecting the Blattodea brain and placing the brain in a microtiter well containing a solution of a compound of interest is a useful model for determining whether the compound of interest permeate the vertebrate BBB. Moreover, the examples above show that a higher compound concentration exposure increases the compound brain concentration of the three compounds.

Example AH

A cut was made through the frontal part of the head of the adult *locusta migratoria*. Each brain was placed for 5 minutes in a microtiter well containing a mixture of Evans Blue. The neural lamella was removed from the brain. No visual signs of Evans Blue were seen in any of the brains, i.e. there is no significant permeation of Evans Blue through the locust brain barrier.

REFERENCES

Abbott, 2005 Dynamics of CNS barriers: evolusion, differtentiation, and modulation. Cell Mol Neurobiol 25: 5-23

Andersson et al (2009), Manuscript under preparation.

Daneman and Barres, 2005 The blood-brain barrier; lessons from moody flies. Cell 123: 9-12

Di, L. and Kerns, E. H. (2003). Profiling drug-like properties in discovery research. *Current Opinion in Chemical Biology* 7, 402-408.

Gaertner, L. S., Murray, C. L., Morris, C. E. (1998). Transepithelial transport of nicotine and vinblastine in isolated malpighian tubules of the tobacco hornworm (*Manduca sexta*) suggests a P-glycoprotein-like mechanism. *The Journal of Experimental Biology* 201, 2637-2645.

Garberg, P. et al. (2005). In vitro models for the blood-brain barrier. *Toxicology in Vitro* 19, 299-334.

Löscher W and Potschka H, 2005 Blood-brain barrier active efflux transporters: ATP binding cassette gene family. NeuroRx 2: 86-98

Mayer F et al., 2009 Evolutionary conservation of vertebrate blood-brain barrier chemoprotective mechanisms in *Drosophila*. J Neuroscience 29: 3538-3550.

Neuwelt et al., 2008; Strategies to advance translation research into brain barriers. Lancet Neurol 7: 84-96.

Nitta et al., 2003 Size-selective loosening of the blood-brain barrier in Claudine-5-deficient mice. J Cell Biol 161: 653-660.

Pardridge, W. M. (2002). Drug and gene targeting to the brain with molecular Trojan horses. *Nature Reviews Drug Discovery* 1, 131-139

Pardridge W. M., 2005 Molecular biology of the blood-brain barrier. Mol Biotechnol 30: 57-70.

Summerfield S G et al., 2007. central nervous system drug disposition: The relationship between in situ brain permeability and brain free fraction. J Pharmacol Exp Ther 322: 205-213

Schinkel et al., 1997 Normal viability and altered pharmacokinetics in mice lacking mdrl-type (drug-transporting) P-glycoproteins. PNAS 94: 4028-4033.

Schinkel, A. H. (1999). P-Glycoprotein, a gatekeeper in the blood-brain barrier. *Advanced Drug Delivery Reviews* 36, 179-194.

Summerfield, S. et al. (2005). Improving the In Vitro Prediction of In Vivo CNS Penetration: Integrating Permeability, Pgp Efflux and Free Fractions in Blood and Brain. *Journal of Pharmacology And Experimental Therapeutics*.

Turksen, K. and Troy, T.-C. (2004). Barriers built on claudins. *Journal of Cell Science* 117, 2435-2447.

Xia, C. Q., Xiao, G., Liu, N., Pimprale, S., Fox, L., Patten, C. J., Crespi, C. L., Miwa, G., Gan, L.-S. (2006). Comparison of Species Differences of P-Glycoproteins in Beagle Dog, Rhesus Monkey, and Human Using ATPase Activity Assays. *Molecular Pharmaceutics* 3 (1), 78-86.

Wu V M and Beitel G J, 2004 A junctional problem a apical proportions: epithelial tube-size control by septate junctions in the *Drosophila* tracheal system. Curr Opin Cell Biol 16: 493-499.

Zlokovic, 2008 The blood-brain barrier in health and chronic neurodegenerative disorders. Neuron 57: 178-201.

The invention claimed is:

1. A method of determining the blood-brain barrier (BBB) penetration of a chemical compound in an insect, said method comprising the steps:
   (i) optionally anesthetizing the insect,
   (ii) fixing the head of the insect,
   (iii) dissecting out the dorsal part of the insect head so as to expose the brain comprising an intact BBB, eyes, antennas and nerve associations,
   (iv) treating the brain comprising the intact BBB while in its cuticle shell ex vivo by placing in a solution of a chemical compound,
   (v) removing the brain from its cuticle shell,
   (vi) washing and homogenizing or ultra sound disintegrating the brain,
   (vii) determining the concentration of the chemical compound in the homogenized brain material; and
   (viii) determining the penetration of the chemical compound through the blood-brain barrier.

2. The method of claim 1, wherein albumin is added to the solution of the chemical compound.

3. The method of claim 1, wherein the concentration of the chemical compound is determined by liquid chromatography/mass spectrometry (LC/MS), LC/MSMS, or HPLC.

4. The method of claim 1, wherein the brain is treated with the solution of the chemical compound for a period of 1-360 minutes.

5. The method of claim 1, wherein the neural lamella of the brain are removed before the brain is homogenised or ultra sound disintegrated.

6. The method of claim 1, wherein the solution of the chemical compound comprises a central nervous system (CNS) drug.

7. The method of claim 4, wherein the brain is treated by placing in the solution of the chemical compound for a period of 5-15 minutes.

8. The method of claim 4, wherein the brain is treated by placing in the solution of the chemical compound for a period of 15 minutes.

9. The method of claim 4, wherein the brain is treated by placing in the solution of the chemical compound for a period of 5 minutes.

10. The method of claim 1, wherein the chemical compound is selected from a compound targeting a central nervous system (CNS) disease or disorder.

11. The method of claim 10, wherein the CNS disease or disorder is selected from the group consisting of Parkinson's Disease, Alzheimer's Disease, Huntington's Disease, a disease with motor neuron inclusions, tauopathies, corticobasal degeneration, epilepsy, pain, and a neuropsychiatric disorder.

12. The method of claim 11, wherein the neuropsychiatric disorder is selected from depression, bipolar disease, schizophrenia, anxiety, aggression, sleep disorders, and drug abuse.

13. The method of claim 1, wherein the chemical compound is selected from the group consisting of a toxic compound and a pesticide.

14. The method of claim 1, wherein the chemical compound is a candidate compound in drug discovery.

* * * * *